United States Patent [19]

Toner

[11] Patent Number: 4,837,169

[45] Date of Patent: Jun. 6, 1989

[54] POLYPYRIDINE FLUORESCENT LABELS FOR IMMUNOASSAY

[75] Inventor: John L. Toner, Webster, N.Y.

[73] Assignee: Eastman Kodak Company, Rochester, N.Y.

[21] Appl. No.: 40,385

[22] Filed: Apr. 20, 1987

Related U.S. Application Data

[60] Continuation-in-part of Ser. No. 7,024, Jan. 27, 1987, which is a division of Ser. No. 825,693, Feb. 3, 1986, Pat. No. 4,637,988, which is a continuation of Ser. No. 279,398, Jul. 1, 1981, abandoned.

[51] Int. Cl.$^4$ .............................................. G01N 21/64
[52] U.S. Cl. ................................. 436/546; 252/301.16; 252/301.17; 252/301.18; 424/7.1; 435/4; 435/7; 436/800; 546/2
[58] Field of Search ................ 436/546, 800; 546/2; 424/7.1; 435/4, 7; 252/301.16, 301.17, 301.18

[56] References Cited

U.S. PATENT DOCUMENTS

| | | | |
|---|---|---|---|
| 4,058,732 | 11/1977 | Wieder | 250/301 X |
| 4,259,313 | 3/1981 | Frank et al. | 424/16 X |
| 4,283,382 | 8/1981 | Frank et al. | 424/16 X |
| 4,352,751 | 10/1982 | Wieder et al. | 560/169 X |

OTHER PUBLICATIONS

*Chemical Abstracts*, 82:38148k (1975) [Busev, A. et al., ZH. Anal. Khim., 1974, 29(8) 1474–7].

Primary Examiner—Richard A. Schwartz
Attorney, Agent, or Firm—John R. Everett

[57] ABSTRACT

There are described stable fluorescent labels comprising a complex of $Eu^{+3}$ and a chelating agent comprising a nucleus which is a triplet sensitizer having a triplet energy greater than that of $Eu^{+3}$ and at least two heteroatom-containing groups which form coordinate complexes with $Eu^{+3}$ and a third heteroatom-containing group or heteroatom in or appended to the triplet sensitizer. Labeled physiologically active materials useful in specific binding assays such as labeled antigens, haptens, antibodies, hormones and the like comprising the stable fluorescent labels having physiologically active materials adsorbed or bonded thereto are also described.

16 Claims, No Drawings

POLYPYRIDINE FLUORESCENT LABELS FOR IMMUNOASSAY

This is a continuation-in-part application of U.S. Ser. No. 007,024, filed Jan. 27, 1987 which is a Rule 60 Divisional of U.S. Ser. No. 825,693 filed Feb. 3, 1986, now U.S. Pat. No. 4,637,988, which is a Rule 62 Continuation of U.S. Ser. No. 279,398 filed July 1, 1981, now abandoned.

FIELD OF THE INVENTION

The present invention relates to novel fluorescent labels and more particularly to fluorescent labels useful for the preparation of specific binding reagents comprising fluorescent labeled physiologically active materials.

BACKGROUND OF THE INVENTION

In specific binding assays, sensitivity is of prime importance due to the generally low analyte levels that are measured. Radioimmunoassay sensitivity limits the assay to measurements of concentration of $10^{-12}M$, and more often only in the $10^{-8}$ to $10^{-10}M$ range. In addition, radiolabels suffer from the drawbacks of short half-life and handling hazards.

In fluorescence spectroscopy assays, a sample containing a fluorescent species to be analyzed is irradiated with light of known spectral distribution within the excitation spectrum of the target fluorescent species. The intensity of the resulting characteristic emission spectrum of the fluorescent target molecules is determined and is related to the number of target molecules.

The sensitivity of fluorescence assays, although theoretically very high, is limited by the presence of background fluorescence. Background signal levels are picked up from competing fluorescent substances, not only in the sample, but also in materials containing the sample. This is an especially serious problem in quantitative measurements of species associated with the samples containing low concentrations of desired target fluorescent molecules such as found in biological fluids. In many situations, it is impossible to reduce the background sufficiently (by appropriate filtration and other techniques known in the art) to obtain the desired sensitivity.

Time resolution offers an independent means of isolating the specific fluorescent signal of interest from nonspecific background fluorescence. Time resolution is possible if the label has much longer-lived fluorescence than the background, and if the system is illuminated by an intermittent light source such that the long-lived label is measurable during the dark period subsequent to the decay of the short-lived background. Such techniques are described in greater detail in German Offenlegungsschrift No. 2,628,158 published Dec. 30, 1976.

The long-lived fluorescence (0.1–5 msec) of the aromatic diketone chelates of certain rare-earth metals, for example, europiumbenzoylacetonate and europiumbenzoyl-trifluoroacetonate, has been known for some time. The chelating agent absorbs light and transfers it to the metal ion, which fluoresces. German OLS No. 2,628,158 describes the use of time resolution in fluorometric immunoassays (FIA) through the use of fluorescent labels whose emissions are long-lived as compared with those of species which produce background interferences in such assays. This publication also provides a useful discussion of the techniques of FIA and its advantage over other immunoassay techniques such as radioimmunoassay (RIA).

The fluorescent immunoreagents described in German OLS No. 2,268,158 comprise at least one member of the immune system, i.e. an antibody or an antigen, "conjugated" with a rare-earth chelate. Such "conjugation" can be achieved in one of two ways:

(1) by labeling, i.e. attaching the rare-earth chelate to the antigen as described in *Fluorescent Antibody Techniques and Their Application* by A. Kawamura, Ed., University Park Press, Baltimore, Maryland, 1969, and then adding antibody to the conjugated antigen whereby the antibody and antigen join in the usual fashion, or (2) by covalent bonding of the antibody of the chelate via a chemical group which binds to both antibodies and the chelates.

The problem with immunoreagents of the type described in German OLS No. 2,268,158 is that the fluorescent labeling species, namely the rare-earth chelates, are quenched, i.e. their fluorescence is extinguished, when contacted with water. This problem, hereinafter referred to as an "aqueous stability" problem, is particularly serious because a principal use for fluorescent labeled immunoreagents is in the assay of aqueous biological liquids such as blood, serum, etc. If aqueous stability could be conferred on these materials, they would be useful as fluorescent labels, for these biological liquids, thus allowing increased fluorescence immunoassay sensitivity by the use of time resolution of signal from background.

Further rare-earth chelates previously used for fluorometric measurements have had undesirable properties such as a low quantum yield for emission, undesirable sensitizer extinction coefficients which result in insufficient fluorescence using small quantities of detectable species, low λmax which renders the determination subject to interference from other components in the sample which are usually in the low λmax range, poor water solubility (most biological fluids are aqueous) and poor stability of the chelate at low concentrations.

SUMMARY OF THE INVENTION

Highly fluorescent compounds have been discovered which are chelates of $Eu^{+3}$ and a chelating agent comprising a nucleus which is a triplet sensitizer having a triplet energy greater than that of $Eu^{+3}$ and at least two heteroatom-containing groups which form chelates (coordinate complexes) with $Eu^{+3}$ and a third heteroatom-containing group or heteroatom which is in the sensitizer or appended to the sensitizer nucleus. The chelates are water-soluble, stable at low concentrations at pH of 7 to 10, highly sensitive, and have favorable molar extinction coefficients (10,000–40,000) and favorable λmax. Accordingly, the present invention provides a class of highly efficient, aqueous-stabilized fluorescent labels for physiologically active materials such as antigens, hormones, antibodies and enzymes.

The chelating agent has the structure

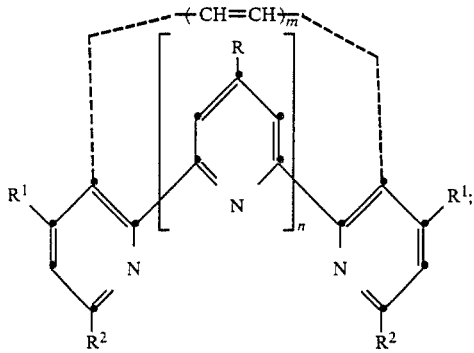

wherein
R represents hydrogen, alkyl, alkoxy, alkylthio, alkylamino, aryl, aryloxy or a heterocyclic group;
R¹ represents hydrogen, alkyl, alkoxy, alkylthio, alkylamino, substituted or unsubstituted aryl or a heterocyclic group;
R² represents carboxy, hydroxy carbonyliminodiacetic acid, methyleneimino diacetic acid, hydrazinylylidene diacetic acid or the salts of such acids;
n is 0 to 4; and
m is 0 to 1
provided that m can be 1 only when n is 0.

Alkyl refers to straight or branched alkyl of about 1 to 12 carbon atoms, preferably 1 to 6 such as methyl, ethyl, isopropyl, 2-ethylhexyl, decyl, etc.

The alkyl portion of alkoxy, alkythio, alkyamino has this same meaning.

Aryl and aryloxy refers to substituted or unsubstituted aryl or aryloxy of about 6 to 20 carbon atoms such as phenyl, naphthyl and phenanthryl including substituted derivatives thereof such as nitrophenyl, hydroxyphenyl, tolyl, xylyl, methoxyphenyl, methylthiophenyl, carboxyphenyl, 5,5-diphenyl-2,4-imidazolidinedione-3-ylmethylphenyl (a diphenylhydantoin substituent on a tolyl group) and the like.

Heterocyclic refers to substituted or unsubstituted heterocyclic groups having 5 to 6 nuclear carbon and hetero atoms such as pyridyl, methylpyridyl, nitropyridyl, methoxypyridyl, oxazolyl, imidazolyl, pyrazolyl, quinolyl, etc.

The alkyl, alkoxy, alkythio, alkyamino, aryl, aryloxy, and heterocyclic groups can be part of, or have appended thereto, proteins for use in biological assays, particularly haptens, enzymes, antibodies, and antigens for example the previously mentioned hydantoin substituent.

The present invention also provides a new class of specific binding reagents, such as antigens, enzymes, hormones and the like bearing these highly useful fluorescent labels.

The reagents are formed by adsorbing or covalently binding the fluorescent labeled antigens, haptens, antibodies, plant lectins, carbohydrates, hormones, enzymes and other such species-specific materials.

DESCRIPTION OF THE PREFERRED EMBODIMENTS $Eu^{+3}$ is complexed with the chelating agent comprising a nucleus which is a triplet sensitizer having a triplet energy greater than that of the lanthanide metal and at least two heteroatom-containing groups and a third heteroatom-containing group or heteroatom which is in or appended to the triplet sensitizer nucleus, each of said two heteroatom-containing groups appended to different carbon atoms of the triplet sensitizer nucleus, said heteroatom-containing groups forming coordinate complexes with $Eu^{+3}$ and said groups being located in said chelating agent such that they and said third heteroatom or heteroatom-containing group are capable of forming a chelate structure with $Eu^{+3}$.

The nucleus of the chelating agent is any triplet sensitizer having the requisite triplet energy. Examples of triplet sensitizers useful herein include heterocyclic and aromatic nitrogen-containing compounds such as quaterpyridines, quinquepyridines, terpyridines and phenanthrolines.

The terpyridines, quaterpyridines and quinquepyridines have the structure

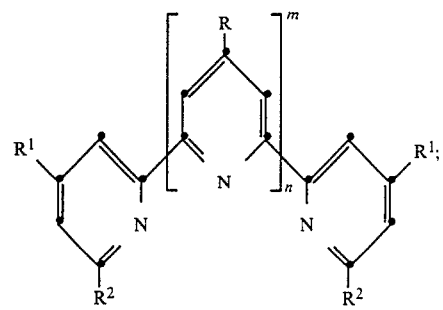

wherein
R represents hydrogen, alkyl, alkoxy, alkylthio, alkylamino, aryl, aryloxy or a heterocyclic group;
R¹ represents hydrogen, alkyl, alkoxy, alkylthio, alkylamino, substituted or unsubstituted aryl or a heterocyclic group;
R² represents carboxy, hydroxy carbonyliminodiacetic acid, methyleneimino diacetic acid, hydrazinylylidene diacetic acid or the salts of such acids; and
n is 0 to 3.

The phenanthrolines have the structure

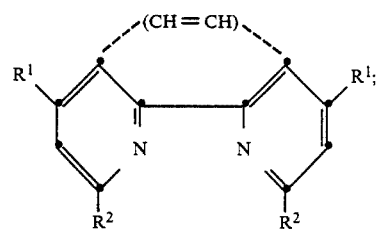

wherein
R¹ represents hydrogen, alkyl, alkoxy, alkylthio, alkylamino, substituted or unsubstituted aryl or a heterocyclic group; and
R² represents carboxy, hydroxy carbonyliminodiacetic acid, methyleneimino diacetic acid, hydrazinylylidene diacetic acid or the salts of such acids.

With europium, the triplet energy must be at least about 47 Kcal.

The complex contains any ratio of $Eu^{+3}$ metal to chelating agent. In preferred embodiments, the mole ratio of $Eu^{+3}$ to chelating agent is from about 1:1 to about 2:1. Especially preferred are complexes having a mole ratio of 1:1.

Eu$^{+3}$ and the chelating agent are easily complexed by merely mixing an aqueous solution of the chelating agent with a Eu$^{+3}$ salt in an aqueous solution of pH 7 to 10. The Eu$^{+3}$ salt is any water soluble salt of the metal such as EuCl$_3 \cdot$6H$_2$O or other halogen salts. The chelate is generally prepared in aqueous solution at a pH of between 8 and 11 and preferably 8 and 9. The chelate optionally is mixed with buffers such as phosphate and borate to produce the optimum pH.

Especially preferred chelating agents are

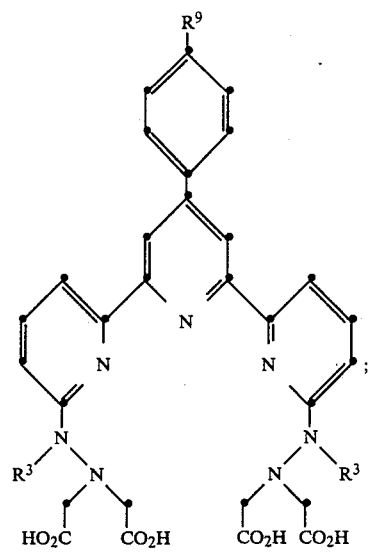

wherein
R$^3$ represents H, or alkyl of about 1 to 8 carbon atoms, and
R$^9$ represents H, —OCH$_3$, —NO$_2$; and

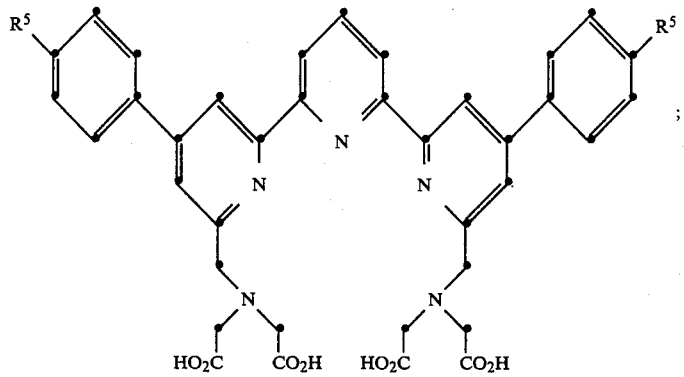

wherein
R$^5$ represents —CH$_3$, NO$_2$, or —OCH$_3$; and

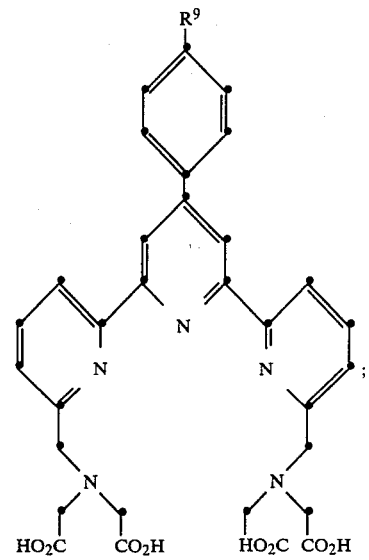

wherein
R$^9$ represents H, —OCH$_3$, —NO$_2$.

The chelate is useful to label a variety of physiologically active materials by binding said materials to the chelate by adsorption or by covalent bonding. Among the physiologically active materials which are labeled in this fashion are enzymes and their substrates, antigens, antibodies, i.e. any substance which is capable, under appropriate conditions, of reacting specifically in some detectable manner with an antibody, carbohydrates, metabolites, drugs, other pharmacalogical agents and their receptors and other binding substances. Specific binding assay reagents are described in U.S. Pat. Nos. 3,557,555; 3,853,987; 4,108,972 and 4,205,058.

Techniques for performing such binding of physiologically active materials to the complexes are those well-known in the art and include simply mixing the materials together.

In specific binding assay methods, a compound having structural similarity to the analyte being determined is herein referred to as the ligand and the labeled compound as the ligand analog. Compounds which specifically recognize the ligands and ligand analogs and bond to them are referred to as receptors.

In performing one such type of assay, the ligand is placed in competition with the ligand analog for binding to the receptor. Unknown concentrations of the ligand are inferred from the measured signal of the labeled, ligand analog. The reaction proceeds as follows:

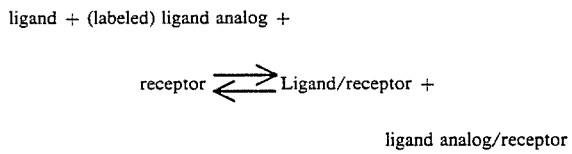

For illustrative purposes, the discussion which follows describes one particular type of specific binding assay technique, a competitive binding fluorescence immunoassay technique.

This system consists of antigen labeled with a fluorescent label of the present invention, unlabeled native antigen (in test sample) and specific antibody whereby there is competition between the unlabeled antigen and the labeled antigen for binding to the antibody.

The greater the concentration of unlabeled antigen from the test sample in the system, the less the labeled antigen will be bound by the antibody. If the concentrations of labeled antigen and antibody are fixed and the only variable is the level of unlabeled antigen, it is possible to determine the unknown level of unlabeled antigen by physically separating the antigen-antibody complex from the remaining free antigen (both labeled and unlabeled) and comparing the fluorescence of the labeled antigen, either free or bound, with a standard curve plotting of the values given by a range of known amounts of the antigen treated in the same manner.

Once prepared as described hereinabove, the fluorescent-labeled, physiologically active species is useful in fluorescent specific binding assays, particularly those which utilize temporal resolution of the specific detecting signal to distinguish from background as described in aforementioned German OLS No. 2,628,158. In this time-resolved mode (i.e. temporal resolution), the sample is excited in an intermittent fashion and information is accepted only during the dark cycle when the long-lived fluorescent label is still emitting strongly but when other sources of fluorescence have decayed. Discontinuous excitation is achieved in a variety of ways, including pulsed laser, mechanical chopping of a continuous excitation beam and moving the sample in and out of the excitation beam. Moreover, discontinuous excitation has the advantage of allowing the use of high radiant power without the absorption of a large amount of energy by the sample, thus diminishing the probability of sample photodegradation.

Examples of such fluorescent specific binding reagents described herein find utility are described in U.S. Pat. Nos. 3,988,943; 4,020,151; 3,939,350; 4,220,450 and 3,901,654.

In a preferred embodiment, the specific binding assay is carried out in a dry analytical element such as described in copending U.S. Pat. No. 4,258,001 granted Mar. 24, 1981 by Pierce and Frank. In this embodiment, the element contains a support and a spreading reagent layer comprised of polymeric beads, and optionally a registration layer. In some cases, the spreading layer is separate from the reagent layer. The spreading, reagent and registration layers optionally comprise the polymeric bead structure. The polymeric beads of the reagent layer have receptors such as antibodies adsorbed to their surfaces.

The chelate label of the present invention is placed above, below, or in the reagent layer in a manner that prevents the specific reaction from occurring prior to sample wetting, or it is spotted onto the element concurrently with or subsequent to the sample. It is only necessary that the labeled ligand analog permeate the element upon wetting subsequently to compete with the unknown amount of ligand in the sample in the formation of the ligandreceptor complex. The assay is performed by fluorimetrically determining the amount of free labeled ligand analog present or the amount of bound labeled ligand analog-receptor complex.

The following non-limiting examples will serve better to illustrate the successful practice of the instant invention.

The syntheses of terpyridines, quaterpyridines and quinquepyridines are similar. The $^1$H-NMR spectra, the mass spectra, and the infrared spectra were consistent for the desired products in each of the following examples.

SCHEME I
Terpyridine compounds are produced according to the following reaction scheme. AcO represents acetoxy, $CH_3COO$.

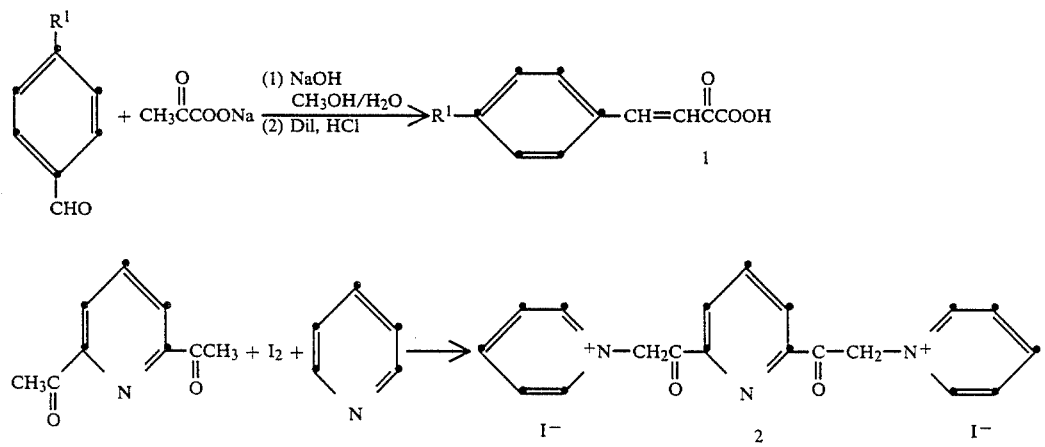

-continued
SCHEME I
Terpyridine compounds are produced according to the following reaction scheme. AcO represents acetoxy, $CH_3COO$.

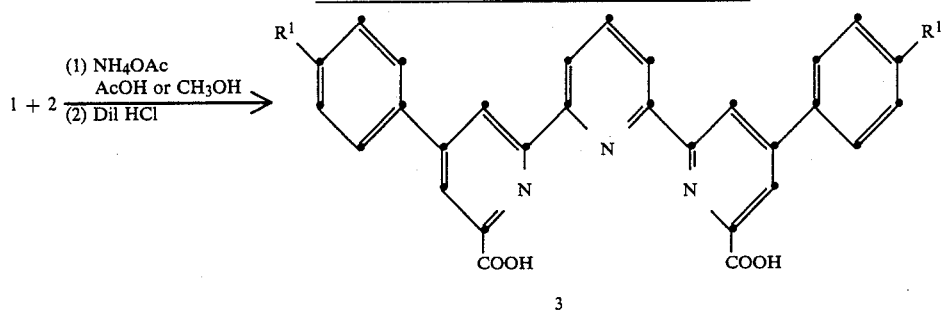

EXAMPLE 1

Preparation of 4,4''-Bis(4-methoxyphenyl)-6,6''-dicarboxy-2,2':6',2''-terpyridine A mixture of compound 1 wherein $R^1$ is methoxy (7.96 g, 34.9 mmol) and the bispyridinium salt 2 (10.0 g, 17.5 mmol) was refluxed for 18 hours in 600 mL of MeOH with 15 g of $NH_4OAc$ according to the procedure of F. Krönke, Synthesis, 1, 1-24 (1976). The solution was filtered and the solid was triturated with hot dilute HCl. The resulting terpyridine diacid was collected by filtration, washed with MeOH then $Et_2O$ (diethyl ether) and dried to give 4.74 g of product as white powder (51%).

Anal. Calcd. for $C_{31}H_{23}N_3O_6 \cdot H_2O$: C, 67.5; H, 4.6; N, 7.6. Found: C, 67.8; H, 4.4; N, 7.5.

Terpyridine compounds 13, 14 and 15 were produced from compound 3 in which $R^1$ was $-CH_3$, according to the following reaction scheme. THF is tetrahydrofuran.

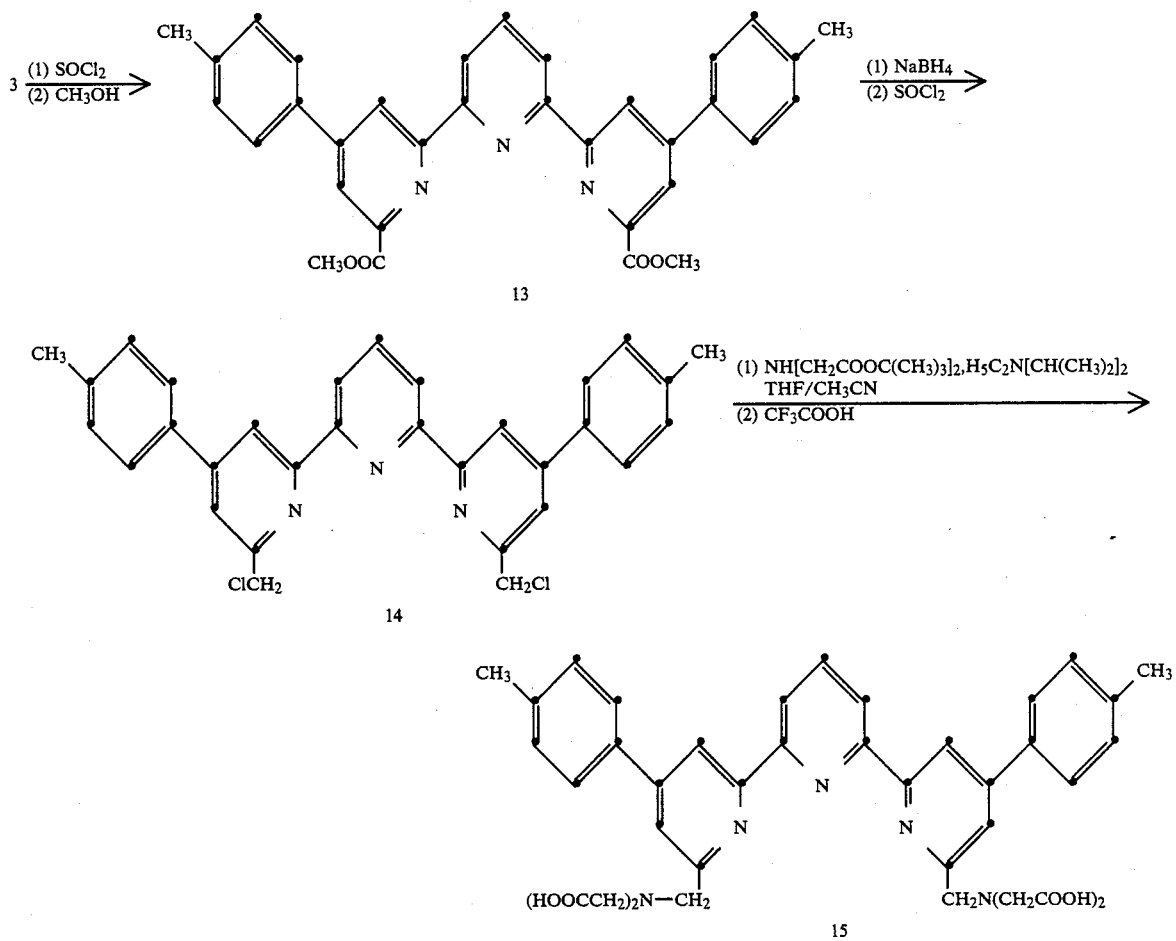

Other representative examples of useful terpyridines are presented in Table 1.

TABLE 1
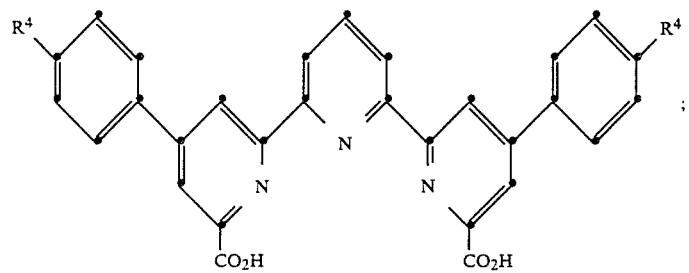
(1)
wherein R[4] represents —H, —SCH$_3$, —OCH$_3$, —CN, —NO$_2$, —CO$_2$CH$_3$, —CH$_3$, etc.;
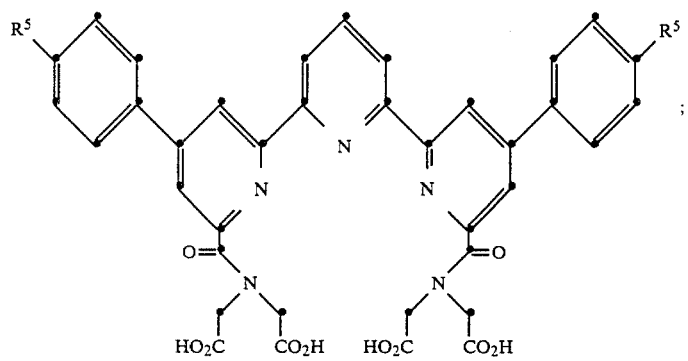
(2)
wherein R[5] represents —CH$_3$, —OCH$_3$, —NO$_2$, etc.;
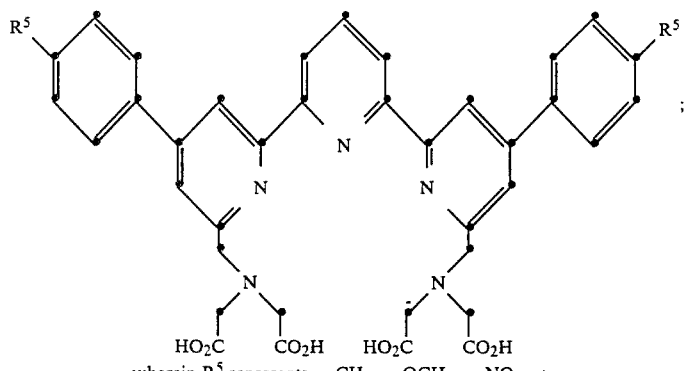
(3)
wherein R[5] represents —CH$_3$, —OCH$_3$, —NO$_2$, etc;
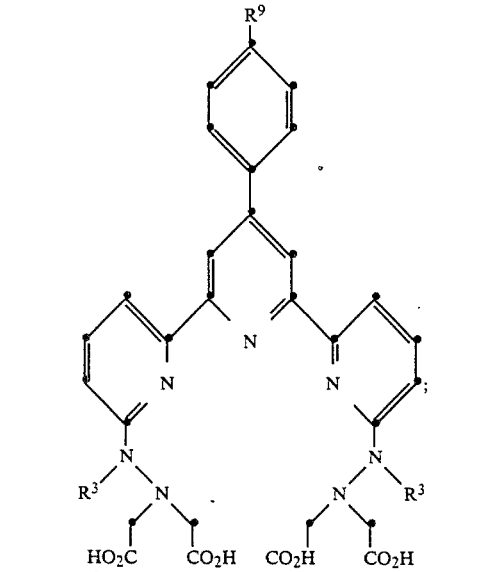
(4)
wherein R[3] represents H, alkyl of 1 to about 8 carbon atoms;
and

TABLE 1-continued
$R^9$ represents H, —OCH$_3$, —NO$_2$, etc.;
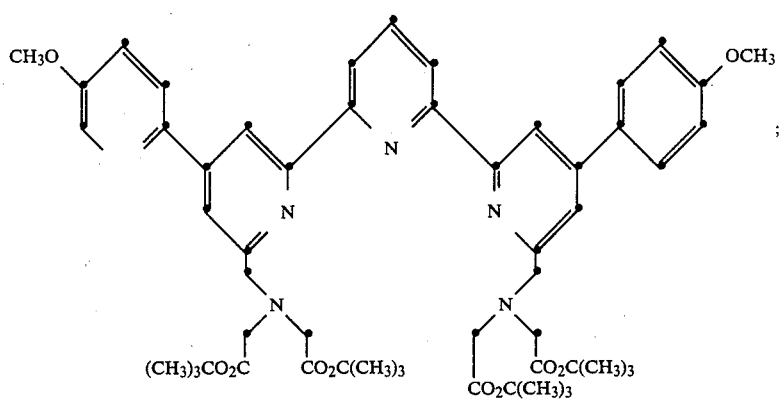
(5)
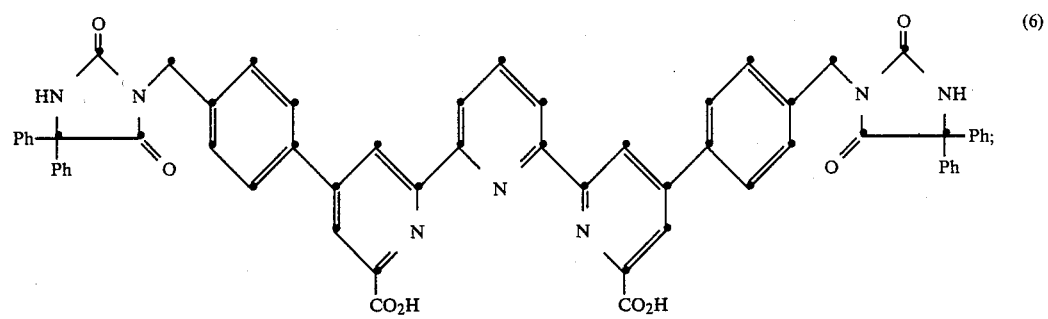
(6)
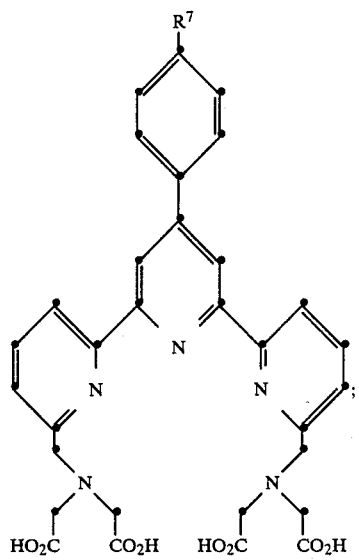
(7)
wherein $R^7$ represents H, —OCH$_3$, —NO$_2$, etc.;

TABLE 1-continued
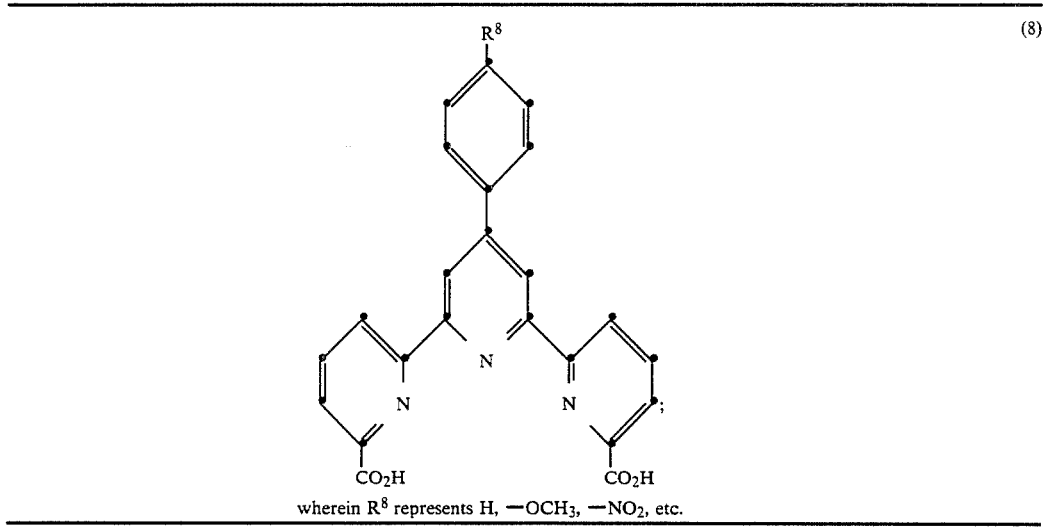
wherein $R^8$ represents H, $-OCH_3$, $-NO_2$, etc.
Quaterpyridine compounds were produced according to the following reaction scheme. Bu is butyl.
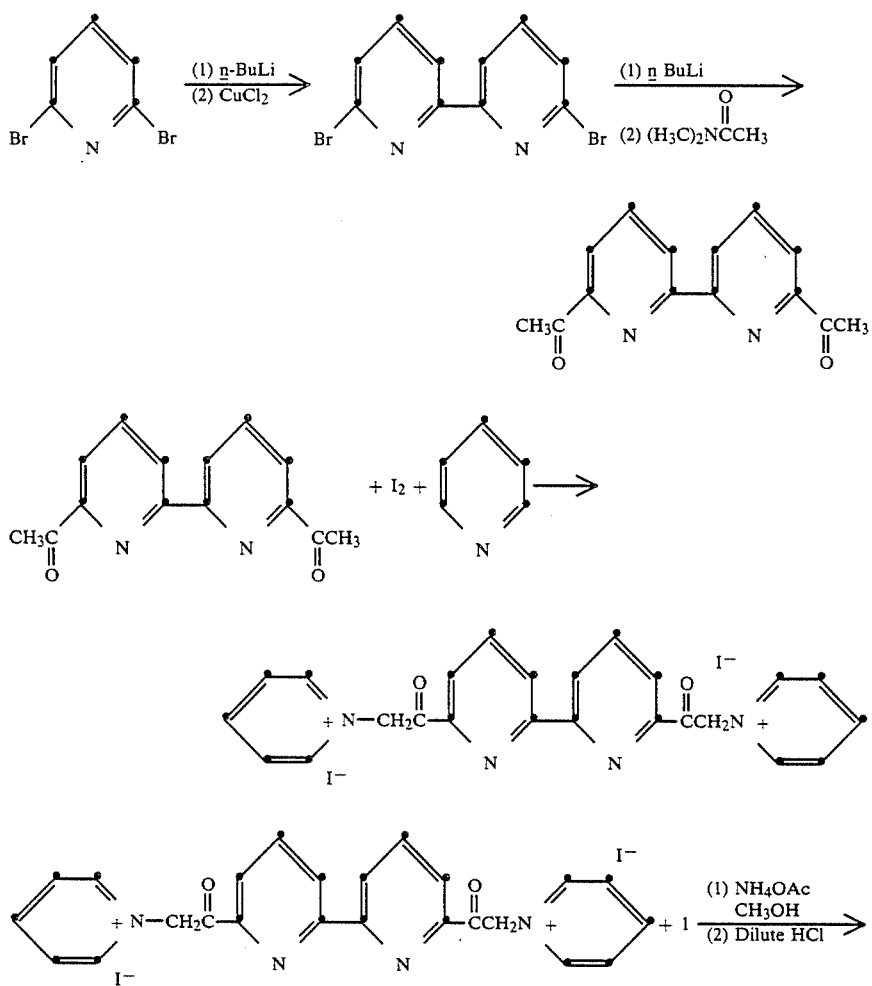

-continued

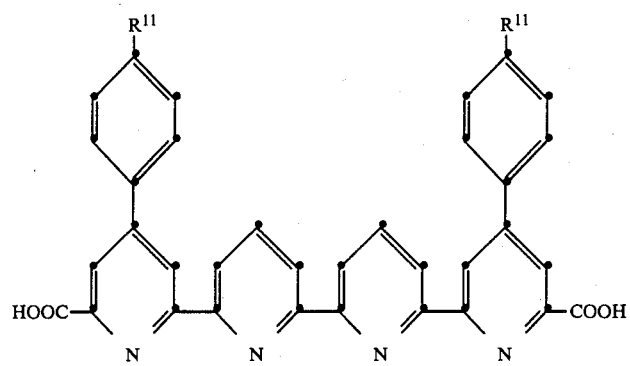

12
12a, $R^{11} = -CH_3$
12b, $R^{11} = -OCH_3$
12c, $R^{11} = -NO_2$

EXAMPLE 2

Preparation of 4,4'''-Bis(4-methylphenyl)-6,6'''-dicarboxy-2,2':6',2"0:6",2'''-quaterpyridine 6,6'-Diacetyl-2,2'-bipyridine was synthesized by the method of J. E. Parks, B. E. Wagner and R. H. Holm, J. Organomet Chem. 56, 53–66 (1973). The bispyridinium iodide was generated by refluxing 2.00 g of the diacetylbipyridine (8.33 mmol) in 50 mL of pyridine with 4.23 g of $I_2$ (16.7 mmol) for 1 hour. The solution was cooled and filtered, and the solid was washed first with pyridine then with $Et_2O$ (diethyl ether) to give, after drying, 4.46 g of the desired product as a sand-colored solid (82%).

Anal. Calcd. for $C_{24}H_{20}I_2N_4O_2$: C, 44.3; H, 3.1; N, 8.6. Found: C, 44.4; H, 3.2; N, 8.8.

The bispyridinium salt (3.00 g, 4.62 mmol) and 1, with $R^{10}$ being methyl, (1.75 g, 9.23 mmol) were combined and refluxed together with 20 g of $NH_4OAc$ in 500 mL of MeOH for 16 hours. The solution was cooled and filtered. The solid was worked up by the method used for 3 (Example 1), then recrystallized from N,N-dimethylformamide (DMF) to give 0.80 g of the titled compound as a cream-colored powder (30%).

Anal. Calcd. for $C_{36}H_{26}N_4O_4 \cdot H_2O$: C, 72.5; H, 4.7; N, 9.4. Found: C, 72.4; H, 4.4; N, 9.3.

Quaterpyridine compounds made by the procedure in Example 2 includes: $R^{11}=-CH_3$ and $-OCH_3$.

Quinquepyridine compounds were prepared according to the following reaction scheme:

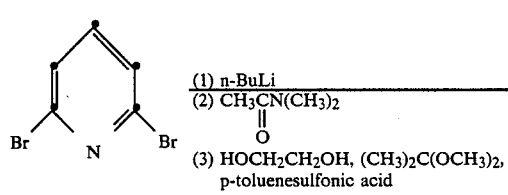

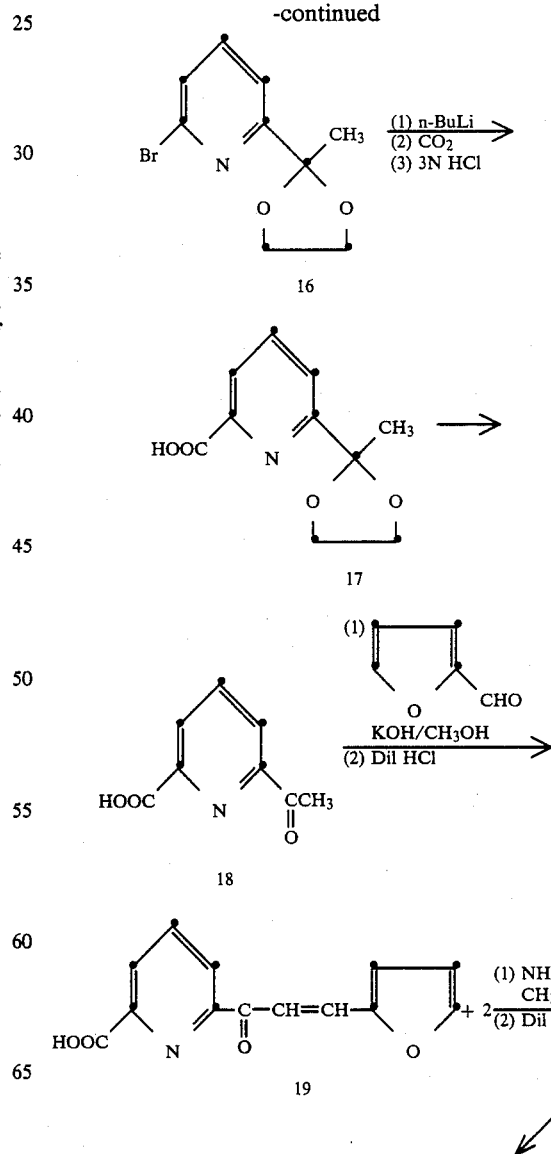

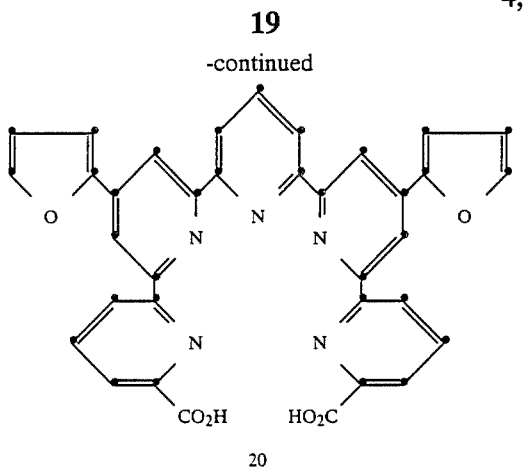

20

EXAMPLE 3

Preparation of
4',4'''-Bis(2-Furyl)-6,6''''-dicarboxy-2,2':6',2'':6'',2''':6''',2'''-quinquepyridine (20)

Compound 16, available by the previously cited Parks et al method, (18.1 g, 74.2 mmol) was dissolved in 400 mL of $Et_2O$ which had been freshly distilled from $LiAlH_4$. With the temperature maintained at $-50°$ C., 35.3 mL of 2.1 M n-BuLi (74.2 mmol) was added dropwise with stirring under $N_2$. After stirring an additional 0.5 hour at $-50°$ C., dry $CO_2$ (g) was bubbled through the solution and the temperature was allowed to rise to 22° C. After 2 hours, the mixture was extracted with dilute aqueous $NaHCO_3$. The organic phase was washed with water and the combined aqueous phase was acidified to pH 2 with HCl then extracted with $CH_2Cl_2$. The $CH_2Cl_2$ phase was washed twice with water then dried over $Na_2SO_4$. Filtration followed by addition of ligroin, and solvent removal gave a yellow solid. Recrystallization from cyclohexane gave 17 as an off-white solid (7.2 g, 46%).

Anal. Calcd. for $C_{10}H_{11}NO_4$: C, 57.4; H, 5.3; N, 6.7. Found: C, 57.2; H, 5.3; N, 6.7.

Compound 17 (6.1 g, 29.2 mmol) was refluxed in 100 mL of 3N HCl for 2 hours under $N_2$. The resulting solution was treated with $NaHCO_3$ to pH 2 then extracted 3 times with $CH_2Cl_2$. The combined organic phase was dried over $Na_2SO_4$, filtered, and evaporated to give 4.4 g of 18 as an off-white powder (91%).

Anal. Calcd. for $C_8H_7NO_3$: C, 58.2; H, 4.3; N, 8.5. Found: C, 58.0; H, 4.3; N, 8.4.

Compound 18 (0.50 g, 3.0 mmol) was refluxed with 2-furaldehyde (0.29 g, 3.0 mmol) in 25 mL of MeOH with 0.2 g of KOH under $N_2$ for 1.5 hours. The solution was poured into 100 mL of aqueous $NaHCO_3$ and extracted with $CH_2Cl_2$ which was discarded. The aqueous phase was acidified and extracted twice with $CH_2Cl_2$. The organic phase was worked up by the procedure used for compound 18 to give chalcone 19 as a light green foam which was pure enough to continue with.

Chalcone 19 (0.60 g, 2.5 mmol) and 2 (0.71 g, 1.2 mmol) were combined and refluxed together with 5 g of $NH_4OAc$ in 100 mL of MeOH for 16 hours. The solution was cooled and filtered and the resulting solid was worked up by the procedure used for the terpyridine diacid 3 in which $R^{10}$ is —$OCH_3$, to give 20 as a tan powder (0.40 g 53%).

Anal. Calcd. for $C_{35}H_{21}N_5O_6 \cdot \frac{1}{2} H_2O$: C, 68.2; H, 3.6; N, 11.4. Found: C, 68.3; H, 3.5; N, 11.5.

A $10^{-6}M$ solution of the quinquepyridine 20 and $EuCl_3 \cdot 6H_2O$ was highly luminescent under long wavelength UV light.

EXAMPLE 4

Preparation of fluorescent chelates with ter-, and quater-pyridines and $Eu^{+3}$ Stock $10^{-5}m$ solutions of terpyridine. $Eu^{+3}$ complexes were prepared by weighing the appropriate amount of the terpyridine into a 1 l volumetric flask; adding 1.00 mL of a stock $10^{-2}M$ $EuCl_3$ solution and then diluting with pH 10 borate buffer. For luminescence vs. concentration studies, the dilutions were carried out with $10^{-5}M$ $Eu^{+3}$ solutions in pH 10 borate buffer. The constant $Eu^{+3}$ concentration forces the terpyridine to remain complexed at low concentrations ($Ka$ = about $5 \times 10^6 M^{-1}$).

Solutions of the quaterpyridine diacid $Eu^{+3}$ complexes were prepared so that the $Eu^{+3}$ concentration was maintained at $10 \times$ the concentration of the quaterpyridine diacid.

For solutions of the terpyridine tetraacid•$Eu^{+3}$ chelates, the $Eu^{+3}$ concentration was maintained at twice the ligand concentration.

The luminescence properties of the chelates are presented in Tables 2, 3 and 4.

TABLE 2

| Luminescence Properties of the Ter- and Quaterpyridine $Eu^{+3}$ Chelates[a] | | | |
|---|---|---|---|
| Compound | $\epsilon$ ($M^{-1} cm^{-1}$)[*] | $\Phi$[*] | Irel[] |
| Table I, compound 1; $R^4 = $ —$CH_3$ | 13,000 (340 nm) | 0.08 | 9.11 |
| Table I, compound 1; $R^4 = $ —$OCH_3$ | 16,000 (340 nm) | 0.07 | 12.5 |
| Example 2, compound 12a; $R^{11} = $ —$CH_3$ | 8,500 (350 nm) | 0.16 | 21.5 |
| Example 2, compound 12b; $R^{11} = $ —$OCH_3$ | 16,000 (350 nm) | 0.14 | 35.7 |
| Example 1, compound 15[****] | 14,000 (339 nm) | — | 18.5 |

[a]Diacid = $10^{-6}$ M, [$Eu^{+3}$] = $10^{-5}$ M.
[*]Refers to the extinction coefficients.
[**]Refers to relative luminescence intensities.
[***]Refers to the relative emission quantum efficiencies.
[****]Contains some diacid impurity.

TABLE 3

Luminescence vs. Concentration for the $Eu^{+3}$ Chelate with Compound 1 of Table I ($R^4 = $ —$CH_3$)

| Concentration of Chelate (M) | pH | Luminesence at 614 nm |
|---|---|---|
| $10^{-6}$ | 10 | 11.46 |

TABLE 3-continued

Luminescence vs. Concentration for the
Eu$^{+3}$ Chelate with Compound 1 of
Table I (R$^4$ = —CH$_3$)

| Concentration of Chelate (M) | pH | Luminesence at 614 nm |
|---|---|---|
| $5 \times 10^{-7}$ | 10 | 7.41 |
| $10^{-7}$ | 10 | 0.86 |
| $5 \times 10^{-8}$ | 10 | 0.35 |
| $3 \times 10^{-8}$ | 10 | 0.23 |
| $10^{-8}$ | 10 | 0.07 |
| $5 \times 10^{-9}$ | 10 | 0.03 |

TABLE 4

Luminescence vs. Concentration for the
Quaterpyridine · Eu$^{+3}$ Chelate
(Example 2, Compound 12b; R$^{11}$ = —OCH$_3$)

| Concentration of Chelate | pH | Luminesence at 616 nm |
|---|---|---|
| $10^{-5}$ | 10 | 365 |
| $10^{-6}$ | 10 | 35.66 |
| $4 \times 10^{-7}$ | 10 | 14.26 |
| $2 \times 10^{-7}$ | 10 | 6.46 |
| $10^{-7}$ | 10 | 2.61 |
| $4 \times 10^{-8}$ | 10 | 0.98 |
| $2 \times 10^{-8}$ | 10 | 0.42 |
| $10^{-8}$ | 10 | 0.24 |
| $4 \times 10^{-9}$ | 10 | 0.09 |

A series of phenanthroline chelating agents were prepared using the following series of reaction schemes. In the chemical structures tBu refers to tertiary butyl.

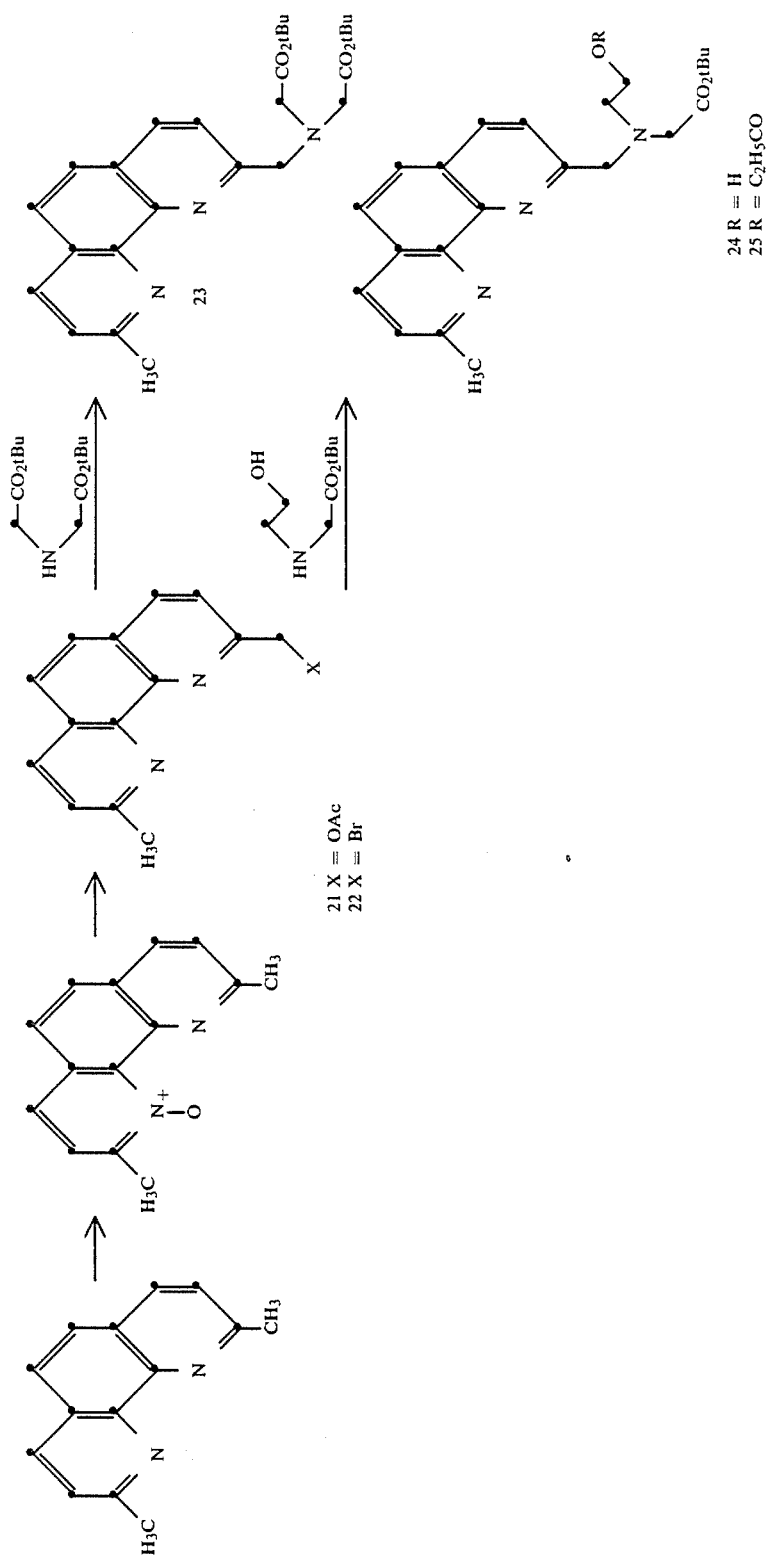

-continued
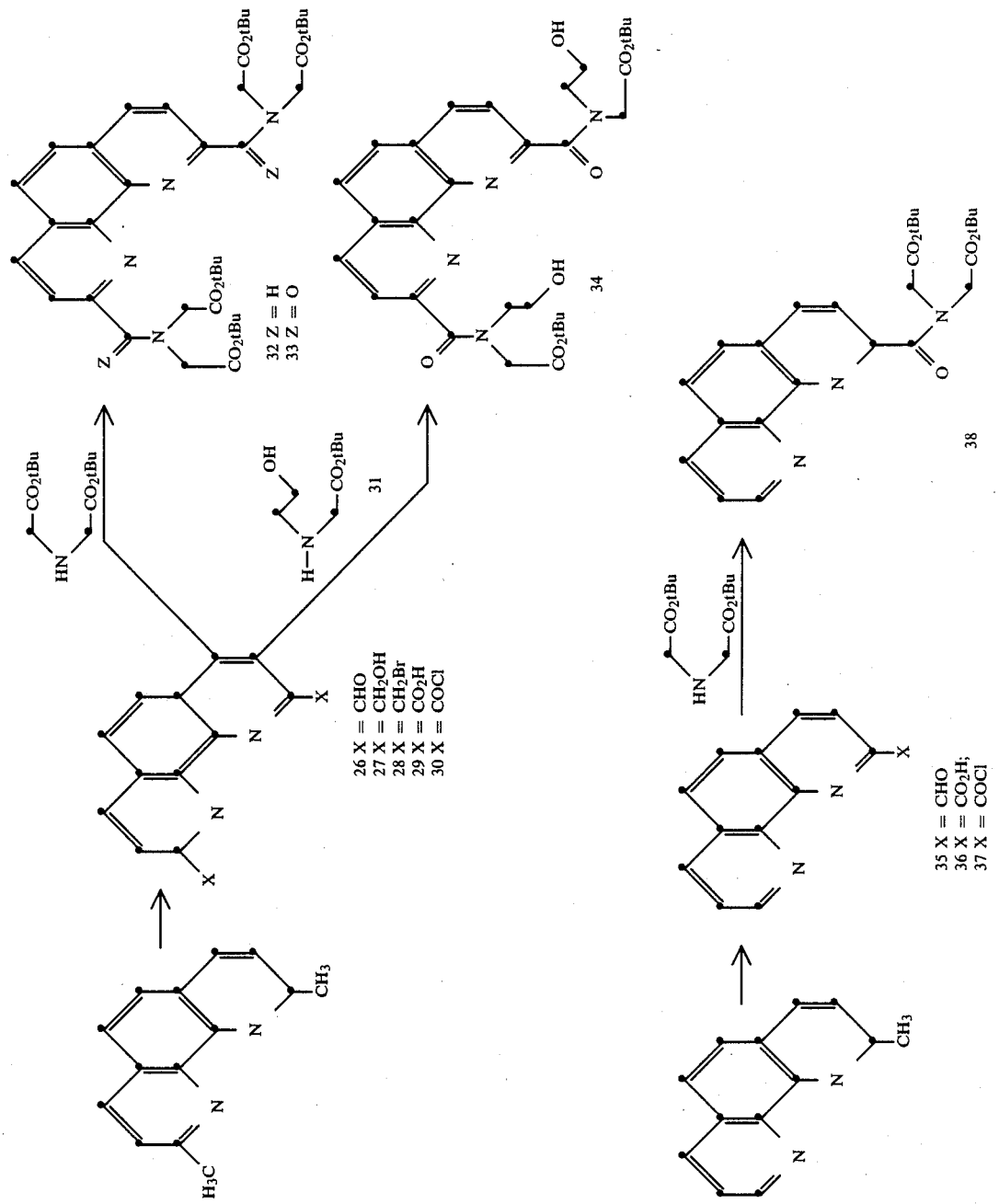

EXAMPLE 5

Preparation of 2-Bromomethyl-9-methyl-1,10-phenanthroline (22).

A mixture of 6.3 g (0.03 mol) of 2,9-dimethyl-1,10-phenanthroline, 6 mL of 30% $H_2O_2$ and 30 mL of trifluoroacetic acid (TFA) was refluxed for 3 hours. The reaction was followed by $^1H$ NMR analysis of the reaction mixture. The volatiles were removed using a rotary evaporator initially and then a vacuum pump to yield a mono N-oxide isolated as a golden syrup that crystallized from $Et_2O$ as the TFA salt. $^1H$ NMR ($CF_3CO_2H$) 2.9 (s, 3H); 3.1(s, 3H); 7.95 (ABq, 1H); 8.1 (ABq, 1H): 8.2 (s, 2H); 8.35 (ABq,1H); 8.9 (ABq,1H).

The N-oxide was dissolved in 90 mL of $Ac_2O$ and then added over 20 min to 250 mL of refluxing $Ac_2O$. $Ac_2O$ is acetic anhydride. After refluxing for an additional 30 minutes, the dark solution was cooled and the $Ac_2O$ removed in vacuo. The crude residue was purified by chromatography on silica gel using $CH_2Cl_2$ to elute 2-acetoxymethyl-9-methyl-1,10-phenanthroline (21). $^1H$ NMR ($CDCl_3$) 2.06 (s, 3H); 3.82 (s, 3H); 5.53 (s, 2H); 7.4 (ABq, 1H J=9 Hz); 7.57 (ABq, 1H, J=9 Hz); 7.62 (s, 2H); 8.0 (Abq, 1H, J=9 Hz); 8.13 (ABq, 1H, J=9 Hz).

The acetate (21) was dissolved in 60 mL of 31% HBr in HoAc and refluxed for 4 hours. After cooling, all the solvent was removed in vacuo. The resulting black residue was suspended in a mixture of $CH_2Cl_2$ and dilute aqueous $NaHCO_3$. Four 200 mL $CH_2Cl_2$ extracts removed the desired bromide from the insoluble material floating at the solvent interface. After drying over $Na_2SO_4$ and removal of the solvent, the dark residual solid was relatively pure phenanthroline (22) containing a trace amount of 2,9-dimethyl-1,10-phenanthroline. The dark impurities were removed by chromatography on silica gel using $CH_2Cl_2$ as the eluent which gave 3.5 g (42%) of 22. $^1H$ NMR ($CDCl_3$) 2.9 (s, 3H); 4.94 (s, 2H); 7.43 (ABq, 1H, J=9 Hz), 7.6 (s, 2H); 7.8 (ABq, 1H, J=9 Hz); 7.97 (ABq, J=9 Hz); 8.1 (ABq, 1H, J=9 Hz).

EXAMPLE 6

Preparation of 2-[di-(t-butoxycarbonylmethyl)-aminomethyl]-9-methyl-1,10-phenanthroline (23)

Part A di-tert-butyl iminodiacetate

A mixture of 5.0 g (38 mmol) of iminodiacetic acid, 4.5 mL (50 mmol) of $HClO_4$ and 100 mL of tert-butyl acetate was stirred for about 20 minutes at 20° C. until the reaction became homogeneous. After standing for 3 days, the solution was poured into 10% aqueous $NaHCO_3$ and extracted three times with 50 mL portions of $CH_2Cl_2$. After drying over $Na_2SO_4$ and removal of solvents using an aspirator, the resulting oil was a mixture of di-tert-butyl iminodiacetate and tert-butyl acetate. The crude product was dissolved in 50 mL of $CH_2Cl_2$ and extracted at 0° C. with 100 mL of 6 M HCl; the aqueous phase was extracted twice with $CH_2Cl_2$ and then poured into ice water saturated with $NaHCO_3$. The resulting alkaline solution was extracted three times with $CH_2Cl_2$. After drying over $Na_2SO_4$, the volatiles were removed to yield 26, isolated as a yellow oil (2.5 g, 27%) which upon standing at −5° C. solidified, $^1H$-NMR ($CDCl_3$ 1.4 (s, 18H); 2.0 (s, 1H); 3.23 (s,4H). Mass spec m/e 245 ($M^+$), 133.

Part B tert-Butyl Ester (23)

A mixture of 900 mg (3.6 mmol) of di-tert-butyl iminodiacetate, 800 mg (2.8 mmol) of bromide (22) and 0.5 g of diisopropylethylamine were stirred in 8 mL of dry DMF at 25° C. for 45 hours. The solution was poured into dilute $NaHCO_3$ in deionized $H_2O$ and extracted 3 times with $CH_2Cl_2$. After drying over $Na_2SO_4$ and solvent removal, by $^1H$ NMR the residue was a 1:1 mixture of 23 and di-tert-butyl iminodiacetate. The material was chromatographed on florisil; a mixture of 40 percent $CH_2Cl_2$ in cyclohexane was used to elute the di-tert-butyl iminodiacetate followed by a mixture of the diacetate and 23; $CH_2Cl_2$ eluted 200 mg of pure 23. $^1H$ NMR ($CDCl_3$) 1.3 (s, 9H); 2.7 (s, 3H);3.35 (s, 4H); 4.3 (s, 2H); 7.4 (ABq, 1H); 7.5 (s, 2H); 7.6 (ABq, 2H); 8.05 (ABq, 1H); 8.05 (m, 2H). Mass spec (field desorption) m/e 451 ($M^+$).

EXAMPLE 7

Preparation of 2-[N,N-di(carboxymethyl)amino-methyl]-9-methyl-1,10-phenanthroline (42 Table II)

A mixture of 200 mg of 23 and 5 mL of trifluoroacetic acid was allowed to stand at 20° C. for 1 hour. In order to monitor the reaction by NMR the solvent was removed under vacuum. A $^1H$ NMR spectrum of the residue residue redissolved in TFA revealed the t-butyl esters had been removed.

EXAMPLE 8

Preparation of 2-(N-tert-butoxycarbonylmethyl-N-hydroxyethylaminomethyl)-9-methyl-1,10-phenanthroline (24)

Part A tert-Butyl N-(2-Hydroxyethyl)glycinate (10)

A mixture of 6 g (0.03 mmol) of tert-butyl bromoacetate in 15 mL of $CH_3CN$ was added over 30 minutes to a 20° C. stirred solution of 30 g of 2-aminoethanol in 30 mL of $CH_3CN$. After stirring for 3 hours, the solvent was removed using a rotary evaporator.

The residue was poured into $H_2O$ and extracted six time with $CH_2Cl_2$. After drying over $Na_2SO_4$ and removal of the $CH_2Cl_2$, 3.1 g (60%) of 10 was obtained as a water-white liquid. $^1H$ NMR 1.35 (s, 9H); 2.1 (broad s, 1H); 2.67 (t, 2H); 3.18 (s, 2H); 3.5 (t, 2H).

Part B

A solution of 3.1 g (18 mmol) of the glycinate from Part A, 4.0 g (11 mmol) of bromide 22 and 2.5 g (19 mmol) of diisopropylethylamine in 15 mL of $CH_2Cl_2$ was stirred for 24 hours at 30° C. The solution was poured into dilute $NaHCO_3$ in deionized $H_2O$ and extracted 3 times with $CH_2Cl_2$. After drying over $Na_2SO_4$ and removal of the solvent, 3 g of residue was obtained which was essentially clean 24. Chromatography on florisil required 1–10% $MeOH/CH_2Cl_2$ to elute pure 24. $^1H$ NMR ($CDCl_3$) 1.44 (s, 9H); 2.83 (s, 3H); 2.94 (t, 2H); 3.4 (s, 2H); 3.6 (t, 2H); 7.4 (ABq, 1H); 7.6 (s, 2H) 7.7 (ABq, 1H); 8.0 (ABq, 1H); 8.1 (ABq, 1H).

EXAMPLE 9

Preparation of 2-(N-tert-butoxycarbonylmethyl-N-propionyloxyethyl-)aminomethyl-9-methyl-1,10-phenanthroline (25)

To a mixture of 100 mg of 24 and 0.3 g of triethylamine in 2 mL of $CH_2Cl_2$ was added 0.2 g of propionyl chloride. The reaction mixture was stirred for 15 hours, poured into dilute $NaHCO_3$ in deionized $H_2O$ and extracted 3 times with $CH_2Cl_2$. After drying over $Na_2SO_4$ and removal of the solvent, the residue was chromatographed on florisil using $CH_2Cl_2$ to elute 110 mg of 25. $^1$H NMR ($CDCl_3$) 1.03 (t, 3H); 1.43 (s, 9H); 2.3 (q, 2H); 2.87 (s, 3H); 3.0 (t, 2H); 3.35 (s, 2H); 4.16 (t, 2H); 4.33 (t, 2H); 7.43 (ABq, 1H, J=9 Hz); 7.65 (s, 2H); 7.97 (ABq, 1H); 8.03 (ABq, 1H); 8.13 (ABq, 1h). Mass spec (FD) m/e 437.

EXAMPLE 10

Preparation of 2,9-Bisformyl-9,10-phenanthroline (26)

As described by C. J. Chandler, L. W. Deady, and J. A. Reiss, *J. Heterocyclic Chem.*, 18, 599 (1981), a mixture of 9.0 g (43.2 mmol) of 2,9-dimethylphenanthroline and 22.5 g (0.2 mol) of selenium dioxide were refluxed in 600 mL of dioxane containing 4% $H_2O$ for 2.5 hours. The hot dark solution was filtered through Celite ®, cooled, and the resulting solid was collected by filtration. After air drying, 8.0 g (80%) of 26 isolated as a yellow solid was obtained. $^1$H NMR (DMSO-$d_6$) 8.2 (s, 2H); 8.32 (ABq, 2H); 8.7 (ABq, 2H) 10.35 (s, 2H).

EXAMPLE 11

Preparation of 2,9-Bis(hydroxymethyl)-1,10-phenanthroline (27)

To a mixture of 2.0 g of dialdehyde 26 in 40 mL of DMF and 5 Ml of ethanol was added 800 mg of $NaBH_4$. The solution was stirred 6 hours at 30° C. then 5 mL of acetone was added. The solvent was removed under vacuum and the residue recrystallized from 50 mL of $H_2O$ to yield 1.7 g of diol (27). $^1$H NMR (DMSO-$d_6$) 4.7 (s, 4H); 5.45 (broad s, 2H); 7.6 (ABq, 2H); 7.7 (s, 2H); 8.25 (ABq, 2H).

EXAMPLE 12

Preparation of 2,9-Bis(bromomethyl)-1,10-phenanthroline (28)

A mixture of 250 mg of diol 27 in 10 mL of 31% HBr in HOAc was refluxed for 3 hours. The solvent of the resulting orange solution was removed in vacuo and the residue was taken up in $CH_2Cl_2$ and dilute aqueous $NaHCO_3$. Due to low solubility, 3 $CH_2Cl_2$ extractions were necessary to leach all the dibromide 28 from the insoluble material. After drying over $Na_2SO_4$ and removal of the solvent, 220 mg (~60%) of 28 was obtained as a dark solid which was pure by NMR. Chromatography on silica gel using $CH_2Cl_2$ eluted 28 as a white solid. $^1$H NMR ($CDCl_3$) 4.87 (s, 4H); 7.63 (s, 2H); 7.83 (ABq, 2H, J=8 Hz); 8.13 (ABq, 2H, J=8 Hz).

EXAMPLE 13

Preparation of 2,9-Bis[N,N-ditert-butoxycarbonyl-methylaminomethyl]-1,10-phenanthroline (32)

A mixture of 220 mg (0.57 mmol) of dibromide 28, 400 mg (1.6 mmol) of di-tert-butyl iminodiacetate, 0.5 g of diisopropylethylamine in 5 mL of 1:1 $CH_2Cl_2/CH_3CN$ was stirred for 15 hours at 25° C. The solution was poured into deionized $H_2O/Na_2HCO_3$ and extracted three times with $CH_2Cl_2$. After drying over $Na_2SO_4$ and solvent removal, the residue was chromatographed on florisil. Residual iminodiacetate and tetraester were eluted with 20–50% $CH_2Cl_2$ in cyclohexane; 5% $MeOH/CH_2Cl_2$ eluted 120 mg of clean 32. $^1$H NMR ($CDCl_3$) 1.30 (s, 18H); 3.42 (s, 8H); 4.23 (s, 2H); 4.33 (s, 2H); 7.60 (s, 2H); 8.05 (ABq, 4H).

EXAMPLE 14

Preparation of 1,10-Phenanthroline-2,9-dicarboxylic acid Chloride (30)

Following the procedure of Chandler et al, referred to in Example 10, a solution of 0.6 g (2.5 mmol) of bisaldehyde 26 in 12 mL of 80% nitric acid was refluxed for 3 hours. Upon cooling, the reaction was poured onto ice and the diacid 29 was collected by filtration. Upon air drying, 0.5 g (75%) of 18 was isolated $^1$H-NMR (DMSO-$d_6$) 8.20 (s, 2H); 8.45 (ABq, 2H); 8.75 (ABq, 2H).

A mixture of 0.5 g of dicarboxylic acid 29 was refluxed in 5 mL of thionyl chloride for 5 hours. The suspension slowly went into solution as the reaction proceeded. The volatiles were removed using a rotary evaporator; the residue was twice dissolved in benzene and stripped to dryness.

$^1$H NMR ($CDCl_3$) 8.05 (s, 2H); 8.45 (s, 4H).

EXAMPLE 15

Preparation of N,N'-Bis(tert-butoxycarbonylmethyl)-N,N'-Bis(2-hydroxyethyl)-1,10-phenanthroline-2,9-diamide (34)

To a 20° C. mixture of 400 mg (4 mmol) of $Et_3N$ and 0.5 g (3 mmol) of tert-butyl N-(2-hydroxyethyl)glycinate in 3 mL of $CH_2Cl_2$ was added 0.3 g (1 mmol) of the bisacid chloride 30. The solution was stirred overnight, poured into $Na_2HCO_3/H_2O$, and extracted three times with $CH_2Cl_2$. After drying over $Na_2SO_4$ and removal of solvent, the residue was chromatographed on florisil. The product came off mainly with $CH_2Cl_2$-5% $MeOH/CH_2Cl_2$ but was contaminated with residual glycinate. This material was slurried in 4 mL of $Et_2O$, 1 mL of petroleum ether was added and the solution decanted from the clean product 20. $^1$H NMR ($CDCl_3$) 1.13 (s, 9H); 1.4 (s, 9H); 3.79 (m, 8H); 4.2 (s, 2H); 4.3 (s, 2H); 7.83 (s, 2H); 7.87 (ABq, 1H); 8.35 (m, 3H). Mass spec (FD) m/e 582.

EXAMPLE 16

Preparation of N,N,N',N'-tetra(tert-butoxycarbonylmethyl)-1,10-phenanthroline-2,9-diamide (33)

A mixture of 3.0 g (11.2 mmol) of diacid 29 and 100 mL of thionyl chloride was refluxed for 16 hours, cooled, and stripped under vacuum. The crude bis(acid chloride) 30, without further purification, was suspended in 200 mL of dry THF to which was added 6.03 g (24.6 mmol) of di-t-butyl iminodiacetate, followed by 3.4 mL (24.6 mmol) of triethylamine. After stirring at 200° C. for 2 hours, the solution was filtered. The filtrate, after concentration, was chromatographed on florisil using a gradient from 25% $EtOAc/CH_2Cl_2$-EtOAc to elute 3 g (37%) of 33 as a clean oil which formed a stiff foam. $^1$H NMR ($CDCl_3$) 1.13 (s, 18H); 1.53 (s, 18H); 4.37 (s, 4H); 5.07 (s, 4H); 7.8 (s, 2H); 8.17

(ABq, 2H, J=8 Hz); 8.27 (ABq, 2H, J=8 Hz). Mass spec (FD) m/e 723 (M+1).

Anal. Calcd. for $C_{38}H_{50}N_4O_{10}$: C, 63.1; H, 7.0; N, 7.8. Found: C, 62.8; H, 7.0; N, 7.9.

EXAMPLE 17

Preparation of N,N,N',N'-tetra(carboxymethyl)-1,10-phenanthroline-2,9-diamide (39, Table 5)

A mixture of 800 mg (1.1 mmol) of 21 in 25 mL of TFA stood for 1 hour at 20° C. Upon removal of the solvent under vacuum and washing of the residue with $Et_2O$, 0.54 g of product (98%) was obtained, isolated as a white powder. $^1H$ NMR ($CDCl_3$/DMSO-$d_6$) 4.32 (s, 4H); 4.84 (s, 4H); 8.05 (ABq, 2H, J=8 Hz); 8.1 (s, 2H); 8.57 (ABq, 2H, J=8 Hz). Anal Calcd. for $C_{22}H_{18}N_4O_{10}$ ½ $H_2O$: C, 52.1; H, 3.8; N, 11.0. Found: C, 52.1; H, 3.9; N, 11.0.

EXAMPLE 18

Preparation of N,N-Bis(tert-butoxycarbonylmethyl)-1,10-phenanthroline-2-carboxylic acid amide (38)

A mixture of 200 mg (0.9 mmol) of 9,10-phenanthroline-2-carboxylic acid in 10 mL of thionyl chloride was refluxed for 6 hours. Although the reaction never became homogeneous, the volatiles were removed using a rotary evaporator. The residue was suspended in benzene and stripped to dryness. The crude product, dissolved in 10 mL of $CH_2Cl_2$, was combined with 240 mg (1 mmol) of di-tert-butyl iminodiacetate followed by 300 mg of triethylamine. After stirring at 30° C. for 24 hours, the reaction was poured into $NaHCO_3$/deionized $H_2O$ and extracted three times with $CH_2Cl_2$, dried over $Na_2SO_4$ and evaporated. The residue was chromatographed on florisil using 1–5% MeOH/$CH_2Cl_2$ to elute 100 mg (24%) of the desired amide 38. $^1H$ NMR ($CDCl_3$) 1.1 (s, 9H); 1.37 (s, 9H); 4.2 (s, 2H); 4.63 (s, 2H); 7.5 (d, 1H); 7.65 (s, 2H); 8.0 (d, 1H); 8.03 (d, 1H); 8.13 (d, 1H); 9.0 (m, 1H). Mass spec (FD) m/e 451.

Hydrolysis proceeded quantitatively by the procedure used for compound 39, Table 5, to give diacid compound 44, Table 5. Other similarly produced compounds are also presented in Table 5.

TABLE 5
Chelating Agents

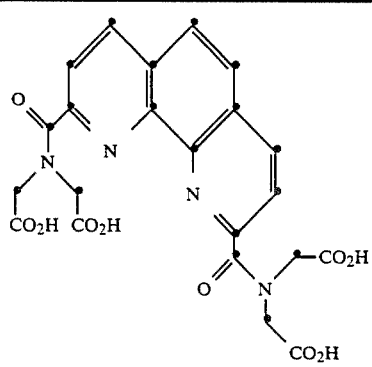

39

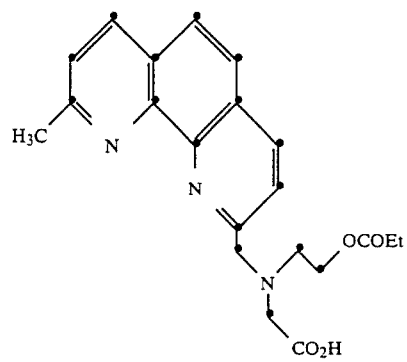

40

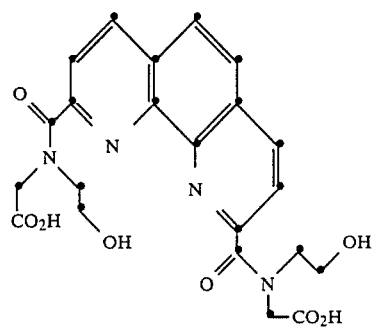

41

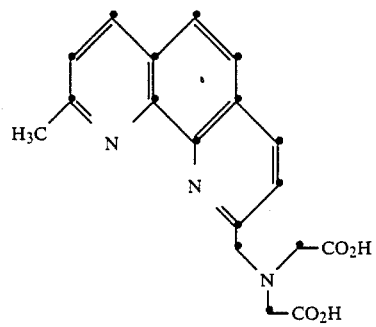

42

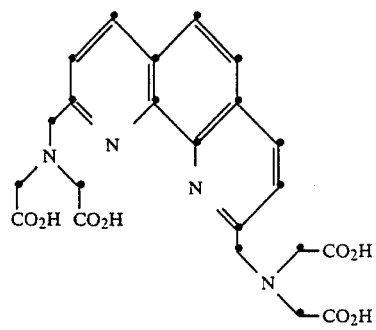

43

TABLE 5-continued

Chelating Agents

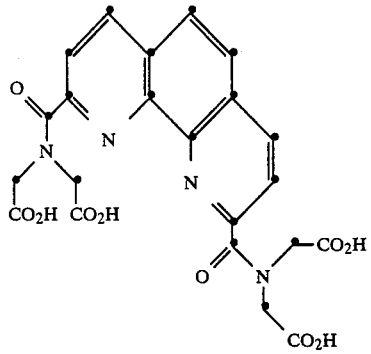

44

EXAMPLE 19

Preparation of phenanthroline tetraacid complexes of $Eu^{+3}$

Stock $10^{-4}$M solutions of the phenanthroline chelating agents were prepared by weighing the appropriate amounts into 1L volumetric flasks, adding 10 mL of $10^{-2}$m $EuCl_3$ solution and diluting with pH 10 borate buffer. In the case of compound 43, Table 5, the solution reached constant luminescence immediately. With compound 39, Table 5, it was necessary to allow the solution to stand for eight days to reach constant luminescence. Relative quantum efficiencies ($\Phi$), absorption maxima and luminescence of the chelates prepared in this example are presented in Tables 6 and 7.

TABLE 6

Quantum Efficiencies and Absorption Maxima for Some $Eu^{+3}$ Chelates in pH 10 Borate Buffer

| | $\Phi Eu^{+3}$ Chelate | $\lambda max$ |
|---|---|---|
| 39, TABLE 5 | 0.02 | 291 |
| 42, TABLE 5 | 0.04 | 277 |

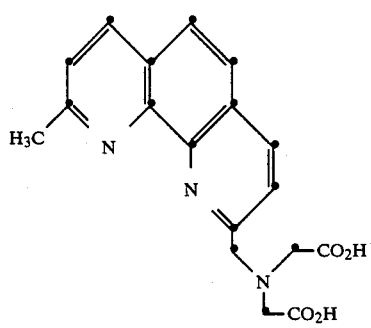

TABLE 6-continued

Quantum Efficiencies and Absorption Maxima for Some $Eu^{+3}$ Chelates in pH 10 Borate Buffer

| | $\Phi Eu^{+3}$ Chelate | $\lambda max$ |
|---|---|---|
| 43, TABLE 5 | 0.06 | 277 |

TABLE 7

Luminescence vs. Concentration for the $Eu^{+3}$ Chelates of Phenanthroline Tetraacids 39 and 43

| Table II Chelating Agent | $-Log[L]^a$ | $Log\ I^b$ |
|---|---|---|
| 39 | 4.1 | −0.48 |
| 39 | 5.2 | −1.50 |
| 43 | 4.2 | 1.36 |
| 43 | 5.2 | 0.42 |
| 43 | 6.2 | −0.60 |
| 43 | 7.2 | −1.52 |

$^a[Eu^{+3}] = [L]$
$^b\lambda$excitation 330 nm, $\lambda$emission 614 nm in pH 8.5 borate buffer The invention has been described in detail with particular reference to preferred embodiments thereof, but it will be understood that variations and modifications can be effected within the spirit and scope of the invention.

What is claimed is:

1. A fluorescent chelate of $Eu^{-3}$ and a chelating agent having the structure

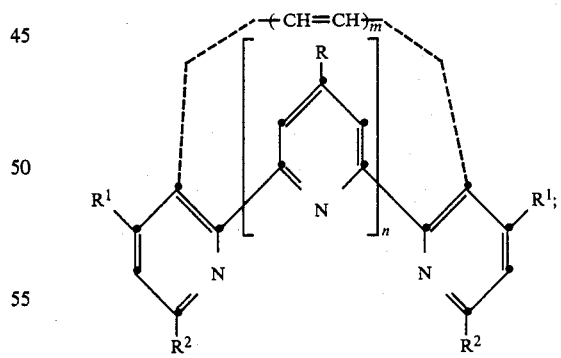

wherein

R represents hydrogen, alkyl, alkoxy, alkylthio, alkylamino, aryl, aryloxy, a heterocyclic group, an enzyme, antigen, or antibody;

$R^1$ represents hydrogen, alkyl, alkoxy, alkylthio, alkylamino, substituted or unsubstituted aryl or a heterocyclic group;

$R^2$ represents carboxy, hydroxy, carbonyliminodiacetic acid, methyleneiminodiacetic acid, hydrazinylylidenediacetic acid or a salt of such acids;

n is 0 to 4; and m is 0 to 1 provided that m can be 1 only when n is 0.

2. The chelate of claim 1 wherein the chelating agent has the structure

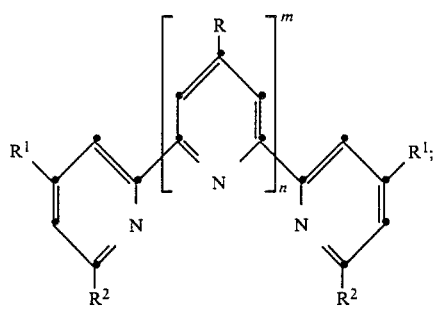

wherein

R represents hydrogen, alkyl, alkoxy, alkylthio, alkylamino, aryl, aryloxy, a heterocyclic group, an enzyme, antigen, or antibody;

$R^1$ represents hydrogen, alkyl, alkoxy, alkylthio, alkylamino, substituted or unsubstituted aryl or a heterocyclic group;

$R^2$ represents carboxy, hydroxy, carbonyliminodiacetic acid, methyleneiminodiacetic acid, hydrazinylylidenediacetic acid or a salt of such acids; and n is 1 to 3.

3. The chelate of claim 1 wherein the chelating agent has the structure

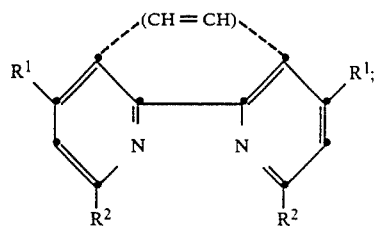

wherein $R^1$ represents hydrogen, alkyl, alkoxy, alkylthio, alkylamino, substituted or unsubstituted aryl or a heterocyclic group; and $R^2$ represents carboxy, hydroxy, carbonyliminodiacetic acid, methyleneimino diacetic acid, hydrazinylylidene diacetic acid or a salt of such acids.

4. The chelate of claim 2 wherein

R represents hydrogen, —$SCH_3$, —$OCH_3$, —CN, —$COOCH_3$ or —$CH_3$;

$R^1$ represents hydrogen, phenyl, methoxyphenyl, tolyl, cyanophenyl, p-methylthiophenyl, methoxycarbonylphenyl, p-(5,5-diphenylimidazolidine-2,4-dion-3-yl)methylphenyl; and $R^2$ represents carboxy, hydroxy, carbonyliminodiacetic acid, methyleneimino diacetic acid, hydrazinylylidene diacetic acid or a salt of such acids.

5. The chelate of claim 3 wherein $R^1$, in the chelating agent, represents hydrogen; and $R^2$ represents carboxy, hydroxy, carbonyliminodiacetic acid, methyleneimino diacetic acid, hydrazinylylidene diacetic acid or a salt of such acids.

6. The chelate of claim 2 wherein the chelating agent has the structure

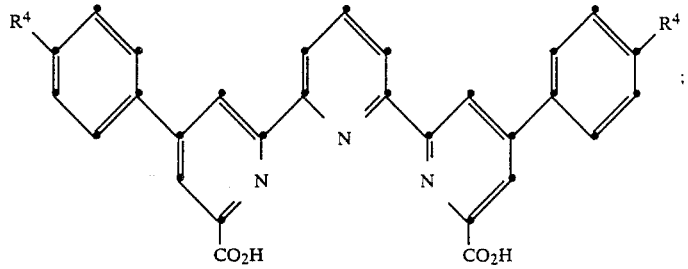

wherein $R^4$ represents —H, —$SCH_3$, —$OCH_3$, —CN, —$NO_2$, —$CO_2CH_3$, —$CH_3$;

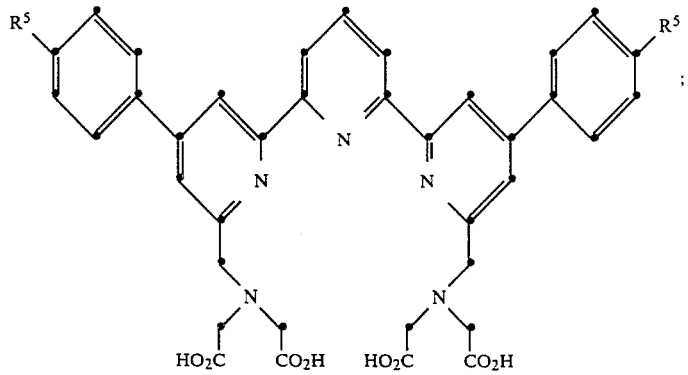

wherein
R[5] represents —CH$_3$, —NO$_2$, or —OCH$_3$;

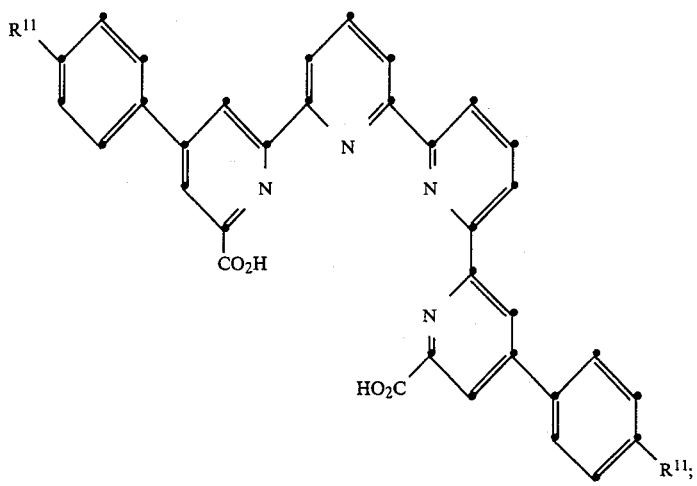

wherein
R[11] represents —CH$_3$, —NO$_2$, —OCH$_3$; or

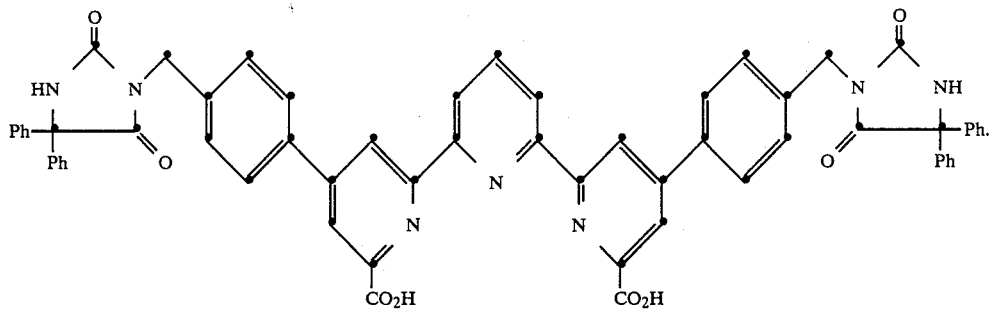

7. The chelate of claim 1, 2, 3, 4, 5 or 6 wherein the mole ratio of Eu$^{-3}$ to the chelating agent is from 1:1 to 2:1.

8. A fluorescently labeled specific binding reagent comprising a physiologically active material adsorbed or bound to a fluorescent label comprising a fluorescent chelate of a Eu$^{-3}$ and a chelating agent having the structure

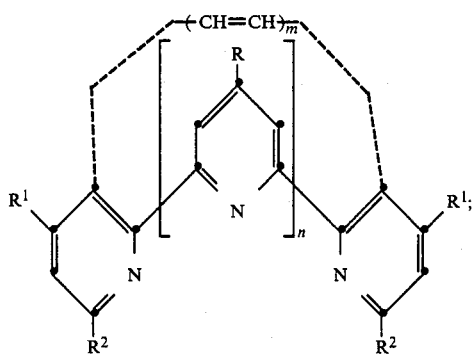

wherein
R represents hydrogen, alkyl, alkoxy, alkylthio, alkylamino, aryl, aryloxy, a heterocyclic group, an enzyme, antigen, or antibody;
R$^1$ represents hydrogen, alkyl, alkoxy, alkylthio, alkylamino, substituted or unsubstituted aryl or a heterocyclic group;
R$^2$ represents carboxy, hydroxy, carbonyliminodiacetic acid, methyleneimino diacetic acid, hydrazinylylidene diacetic acid or a salt of such acids;
n is 0 to 4; and
m is 0 to 1
provided that m can be 1 only when n is 0.

9. The binding reagent of claim 8 wherein the chelating agent has the structure

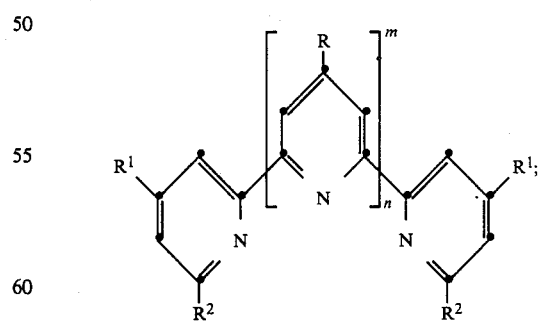

wherein
R$^1$ represents hydrogen, alkyl, alkoxy, alkylthio, alkylamino, substituted or unsubstituted aryl or a heterocyclic group;
R$^2$ represents carboxy, hydroxy, carbonyliminodiacetic acid, methyleneimino diacetic acid, hydrazinylylidene diacetic acid or a salt of such acids; and n is 1 to 3.

10. The binding reagent of claim 8 wherein the chelating agent has the structure

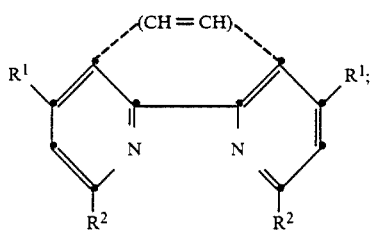

wherein

R¹ represents hydrogen, alkyl, alkoxy, alkylthio, alkylamino, substituted or unsubstituted aryl or a heterocyclic group; and R² represents carboxy, hydroxy, carbonyliminodiacetic acid, methyleneimino diacetic acid, hydrazinylylidene diacetic acid or a salt of such acids.

11. The binding reagent of claim 9 wherein

R¹ represents hydrogen, phenyl, methoxyphenyl, tolyl, cyanophenyl, p-methylthiophenyl, methoxycarbonylphenyl or p-(5,5-diphenylimidazolidine-2,4-dion-3-yl)methylphenyl; and R² represents carboxy, hydroxy, carbonyliminodiacetic acid, methyleneimino diacetic acid, hydrazinylylidene diacetic acid or a salt of such acids.

12. The binding reagent of claim 9 wherein the chelating agent has the structure

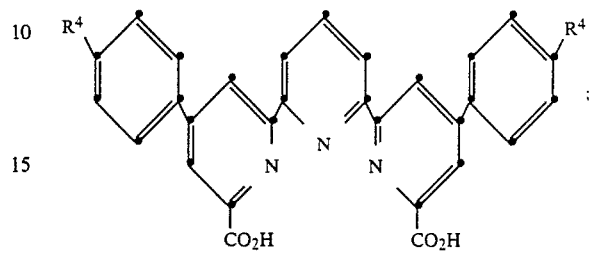

wherein $R^4$ represents —H, —SCH$_3$, —OCH$_3$, —CN, —NO$_2$, —CO$_2$CH$_2$, —CH$_3$;

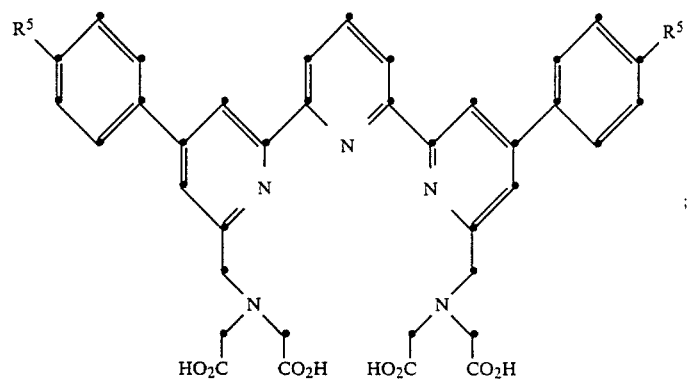

wherein $R^5$ represents —CH$_3$, —NO$_2$, or —OCH$_3$;

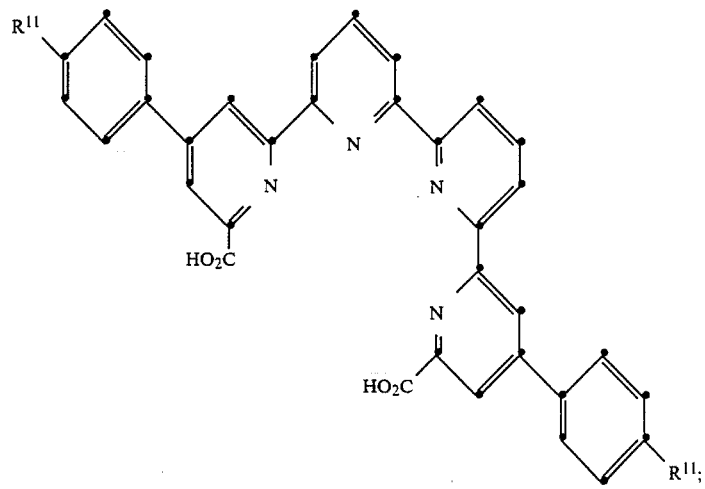

wherein $R^{11}$ represents —CH$_3$, —NO$_2$, —OCH$_3$; or

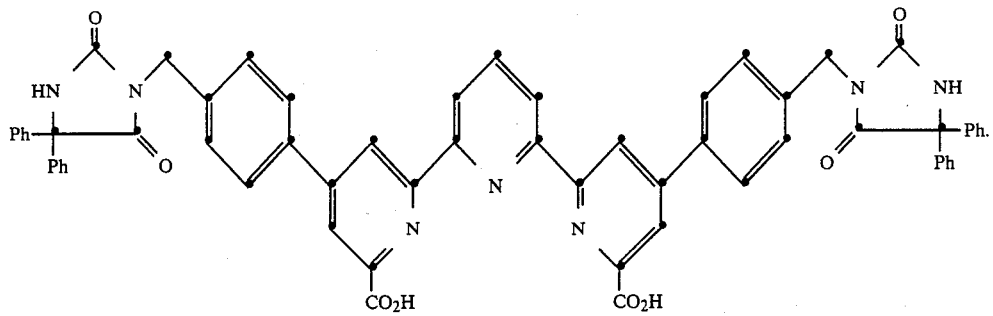

13. The labeled specific binding reagent of claim 8, 9, 10, 11 or 12 wherein the physiologically active material is selected from the group consisting of antibodies, antigens, haptens, enzymes, enzyme substrates, metabolites, vitamins, hormones, hormone receptors, cell surface receptors and lectins.

14. The labeled specific binding reagent of claim 8, 9, 10, 11, or 12 wherein the mole ratio of $Eu^{+3}$ to the chelating agent is from 1:1 to 2:1.

15. A method of labeling physiologically active materials comprising adsorbing or covalently binding said material to a chelate of a $Eu^{+3}$ and a chelating agent having the structure

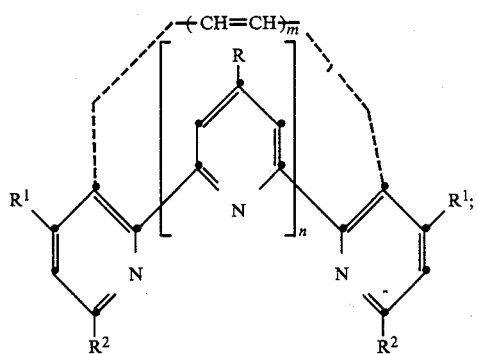

wherein
- R represents hydrogen, alkyl, alkoxy, alkylthio, alkylamino, aryl, aryloxy, a heterocyclic group, an enzyme, antigen, or antibody;
- $R^1$ represents hydrogen, alkyl, alkoxy, alkylthio, alkylamino, substituted or unsubstituted aryl or a heterocyclic group;
- $R^2$ represents carboxy, hydroxy, carbonyliminodiacetic acid, methyleneimino diacetic acid, hydrazinylylidene diacetic acid or a salt of such acids;
- n is 0 to 4; and
- m is 0 to 1 provided that m can be 1 only when n is 0.

16. In a method for performing an immunoassay comprising the steps of
(a) fluorescently labeling a ligand of interest, a derivative of said ligand or some other molecular entity, to produce a fluorescently labeled immunologically binding ligand analog of said ligand of interest;
(b) adding a known amount of said fluorescently labeled ligand analog and an unknown amount of ligand to be assayed to a receptor which is capable of binding with said fluorescently labeled ligand analog and also is capable of binding with said ligand to be assayed; and
(c) determining the unknown amount of said ligand to be assayed by measuring the fluorescence of said fluorescently labeled ligand analog bound to said receptor or by measuring the fluorescence of said fluorescently labeled ligand analog remaining unbound, the improvement wherein the labeled ligand analog comprises ligand adsorbed or covalently bound to a fluorescent label comprising a fluorescent chelate of a lanthanide metal and a chelating agent having the structure

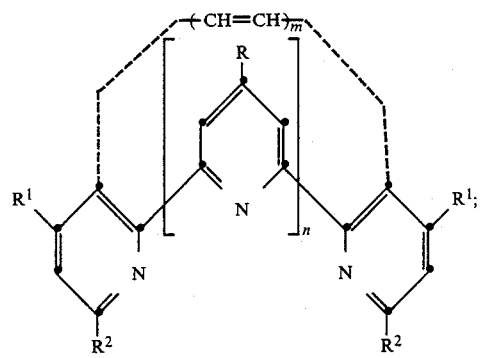

wherein
- R represents hydrogen, alkyl, alkoxy, alkylthio, alkylamino, aryl, aryloxy or a heterocyclic group;
- $R^1$ represents hydrogen, alkyl, alkoxy, alkylthio, alkylamino, substituted or unsubstituted aryl or a heterocyclic group;
- $R^2$ represents carboxy, hydroxy, carbonyliminodiacetic acid, methyleneimino diacetic acid, hydrazinylylidene diacetic acid or a salt of such acids;
- n is 0 to 4; and
- m is 0 to 1 provided that m can be 1 only when n is 0.

* * * * *